US00PP19935P2

(12) United States Plant Patent
Bloom

(10) Patent No.: US PP19,935 P2
(45) Date of Patent: Apr. 21, 2009

(54) ***BUDDLEJA* PLANT NAMED 'BUTTERFLY HEAVEN'**

(50) Latin Name: *Buddleja davidii*
Varietal Denomination: Butterfly Heaven

(76) Inventor: Adrian Bloom, Foggy Bottom, Bressingham, Diss, Norfolk IP22 2AB (GB)

( * ) Notice: Subject to any disclaimer, the term of this patent is extended or adjusted under 35 U.S.C. 154(b) by 0 days.

(21) Appl. No.: 12/151,755

(22) Filed: May 8, 2008

(51) Int. Cl.
*A01H 5/00* (2006.01)

(52) U.S. Cl. ..... Plt./242
(58) Field of Classification Search ..... Plt./242
See application file for complete search history.

*Primary Examiner*—Annette H Para
*Assistant Examiner*—Georgia Helmer
(74) *Attorney, Agent, or Firm*—C. A. Whealy

(57) ABSTRACT

A new and distinct cultivar of *Buddleja* plant named 'Butterfly Heaven', characterized by its upright and outwardly spreading plant habit; freely flowering habit; large, fragrant and light lavender-colored flowers with golden orange-colored centers; and good garden performance.

1 Drawing Sheet

Botanical designation: *Buddleja davidii.*
Cultivar denomination: 'Butterfly Heaven'.

BACKGROUND OF THE INVENTION

The present invention relates to a new and distinct cultivar of *Buddleja,* botanically known as *Buddleja davidii* and hereinafter referred to by the name 'Butterfly Heaven'.

The new *Buddleja* is a product of a planned breeding program conducted by the Inventor in Bressingham, United Kingdom. The objective of the breeding program was to create new *Buddlejas* with attractive flower coloration.

The new *Buddleja* originated from an open-pollination in 2000 in Bressingham, United Kingdom, of *Buddleja davidii* 'Pink Delight', not patented, as the female, or seed, parent with an unknown selection of *Buddleja davidii* as the male, or pollen, parent. The new *Buddleja* was discovered and selected by the Inventor as a single flowering plant within the progeny of the stated open-pollination in a controlled greenhouse environment in Bressingham, United Kingdom in 2000.

Asexual reproduction of the new *Buddleja* by cuttings in a controlled greenhouse environment in Bressingham, United Kingdom since May, 2001, has shown that the unique features of this new *Buddleja* are stable and reproduced true to type in successive generations.

SUMMARY OF THE INVENTION

The new *Buddleja* has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Butterfly Heaven'. These characteristics in combination distinguish 'Butterfly Heaven' as a new and distinct cultivar of *Buddleja:*

1. Upright and outwardly spreading plant habit.
2. Freely flowering habit.

3. Large, fragrant and light lavender-colored flowers with golden orange-colored centers.
4. Good garden performance.

Plants of the new *Buddleja* differ from plants of the female parent in the following characteristics:

1. Plants of the new *Buddleja* are more compact than plants of 'Pink Delight'.
2. Plants of the new *Buddleja* and 'Pink Delight' differ in flower color as plants of 'Pink Delight' have pink-colored flowers.

Plants of the new *Buddleja* can be compared to plants of *Buddleja davidii* 'Peacock', not patented. In side-by-side comparisons, plants of the new *Buddleja* and 'Peacock' differed in the following characteristics:

1. Plants of the new *Buddleja* were more compact than plants of 'Peacock'.
2. Plants of the new *Buddleja* and 'Peacock' differed in flower color as plants of 'Peacock' had pink-colored flowers.

BRIEF DESCRIPTION OF THE PHOTOGRAPHS

The accompanying colored photographs illustrate the overall appearance of the new *Buddleja,* showing the colors as true as it is reasonably possible to obtain in colored reproductions of this type. Colors in the photographs may differ slightly from the color values cited in the detailed botanical description which accurately describe the colors of the new *Buddleja.*

The photograph at the bottom of the sheet comprises a side perspective view of a typical flowering plant of 'Butterfly Heaven' grown in a container.

The photograph at the top of the sheet is a close-up view of a typical inflorescence of 'Butterfly Heaven'.

DETAILED BOTANICAL DESCRIPTION

The aforementioned photographs and following observations, measurements and values describe plants grown in Lancaster, Pa. under commercial practice during the summer and early autumn in a polyethylene-covered greenhouse with day temperatures ranging from 21° C. to 38° C. and night temperatures ranging from 18° C. to 29° C. Plants were 18 weeks from planting when the photographs and description were taken. In the following description, color references are made to The Royal Horticultural Society Colour Chart, 2001 Edition, except where general terms of ordinary dictionary significance are used.

Botanical classification: *Buddleja davidii* 'Butterfly Heaven'.

Parentage:

*Female, or seed, parent.*—*Buddleja davidii* 'Pink Delight', not patented.

*Male or pollen parent.*—Unknown selection of *Buddleja davidii,* not patented.

Propagation:

*Type.*—By cuttings.

*Time to initiate roots plant, summer.*—About 10 days at 21° C. to 25° C.

*Time to produce a rooted plant, summer.*—About two months at 21° C. to 25° C.

*Time to produce a rooted plant, winter.*—About six months at 5° C. to 8° C.

*Root description.*—Fibrous; white, close to 158B, in color.

*Rooting habit.*—Freely branching; moderately dense.

Plant description:

*Plant form/habit.*—Deciduous perennial shrub. Upright and outwardly spreading habit; broad inverted triangle; vigorous growth habit.

*Plant height.*—About 64 cm.

*Plant width* (*spread*).—About 67 cm.

*Lateral branches.*—Quantity: About six main branches each with about four to six lateral branches per plant. Length: About 48 cm. Diameter: About 8 mm. Internode length: About 3 cm to 5.5 cm. Strength: Strong. Texture, developing stems: Tomentose. Texture, mature stems: Smooth, glabrous. Color, developing: Close to 194A. Color, mature: Close to 199A to 199B.

Foliage description:

*Arrangement.*—Opposite, simple.

*Length.*—About 8.4 cm.

*Width.*—About 2.2 cm.

*Shape.*—Elliptical.

*Apex.*—Acuminate.

*Base.*—Attenuate.

*Margin.*—Serrulate.

*Texture, upper and lower surfaces.*—Pubescent.

*Venation pattern.*—Pinnate, reticulate.

*Color.*—Developing leaves, upper surface: Close to 137A. Developing leaves, lower surface: Close to 191B. Fully expanded leaves, upper surface: Close to 139A; venation, close to 147C. Fully expanded leaves, lower surface: Close to 191A; venation, close to 148C.

*Petiole.*—Length: About 4 mm. Diameter: About 2 mm. Texture, upper and lower surfaces: Pubescent. Color, upper and lower surfaces: Close to 147C.

Flower description:

*Flower type/habit.*—Single rotate and salverform flowers arranged in compound terminal panicles; flowers face upright and outward. Panicles roughly conical in shape. Freely flowering habit with about 1,100 flower buds and flowers developing per inflorescence.

*Fragrance.*—Moderately fragrant; sweet.

*Natural flowering season.*—Continuously flowering throughout the summer in Pennsylvania. Flowers not persistent.

*Postproduction longevity.*—Flowers last about five days on the plant.

*Flower buds.*—Height: About 1 cm. Diameter: About 1.5 mm. Shape: Narrowly lanceolate. Color: Close to 98C.

*Inflorescence height.*—About 14 cm to 15 cm.

*Inflorescence diameter.*—About 7 cm.

*Flower diameter.*—About 7 mm.

*Flower depth.*—About 1.1 cm.

*Petals.*—Quantity per flower: Typically four in a single whorl; petals fused into a narrow tube. Length: About 3 mm. Lobe width: About 3 mm. Shape: Roughly spatulate. Apex: Emarginate. Margin: Sinuate, erose. Texture, upper and lower surfaces: Smooth, glabrous. Color: Developing petals, upper surface: Close to 94C. Developing petals, lower surface: Close to 94D. Fully expanded petals, upper surface: Close to 94D; towards the center, close to 20A; throat, close to 25A. Color becoming closer to 92C with development. Fully expanded petals, lower surface: Close to 92B; tube, close to 23C to 23D. Color becoming closer to 92D with development.

*Sepals.*—Quantity per flower: Typically four in a single whorl, fused towards the base; campanulate calyx. Length: About 3 mm. Width: About 1 mm. Shape: Lanceolate. Apex: Acute. Margin: Entire. Texture, upper surface: Smooth, glabrous. Texture, lower surface: Pubescent. Color, upper surface: Close to 194A. Color, lower surface: Close to 194B.

*Peduncles.*—Length: About 2.3 cm. Diameter: About 2.5 mm. Angle: Mostly erect. Strength: Strong. Texture: Pubescent. Color: Close to 194B.

*Pedicels.*—Length: About 7 mm. Diameter: About 1 mm. Angle: About 35° to 45° from vertical. Strength: Strong. Texture: Pubescent. Color: Close to 194B.

*Reproductive organs.*—Stamens: Quantity per flower: Typically four; filaments adnate to the corolla tube. Anther shape: Lanceolate. Anther length: About 1.5 mm. Anther color: Close to 145C. Pollen amount: Scarce. Pollen color: Close to 155A. Pistils: Quantity per flower: One. Pistil length: About 7 mm. Stigma shape: Rounded. Stigma color: Close to 146D. Style length: About 2.5 cm. Style color: Close to 145B. Ovary color: Close to 146C.

*Seed/fruit.*—Seed and fruit development have not been observed.

Disease/pest resistance: Plants of the new *Buddleja* have been not been observed to be resistant to pathogens and pests common to *Buddleja.*

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Butterfly Heaven' as illustrated and described.

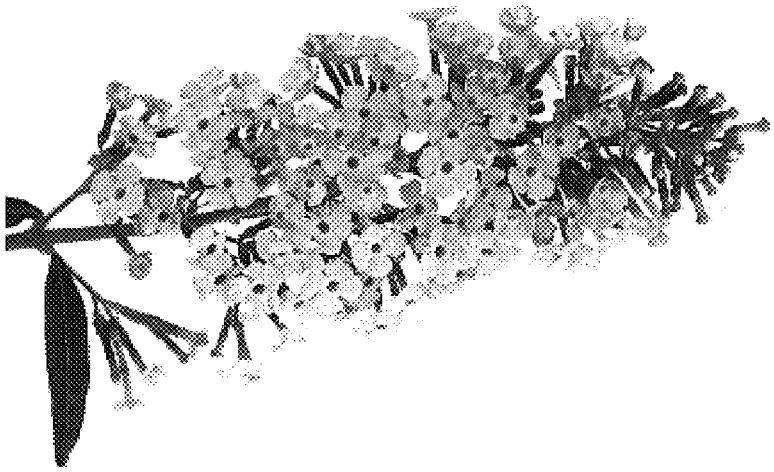
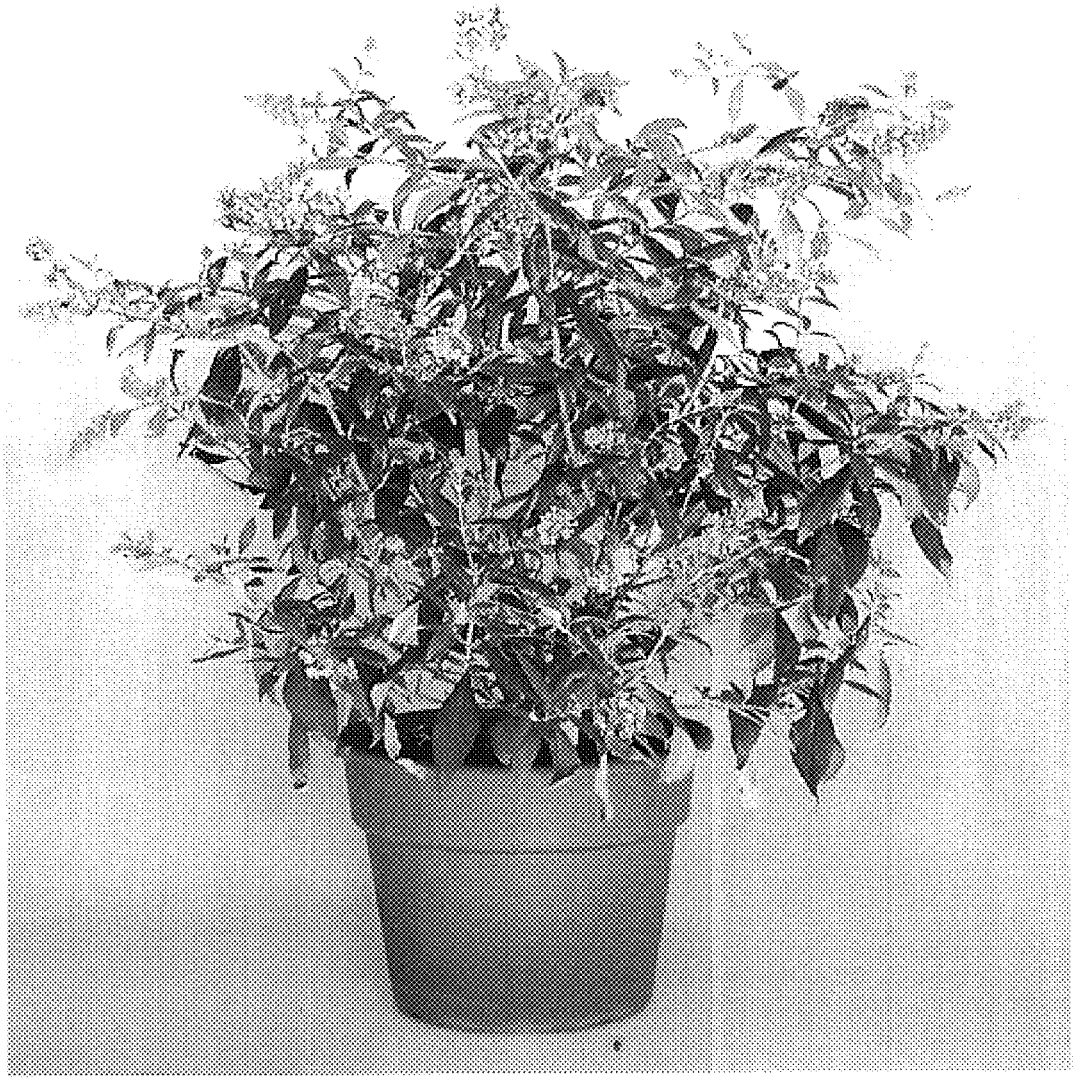

* * * * *